US012127838B2

(12) United States Patent
Olsen et al.

(10) Patent No.: US 12,127,838 B2
(45) Date of Patent: Oct. 29, 2024

(54) SELF-CONTAINED MINIMAL ACTION INVASIVE BLOOD CONSTITUENT SYSTEM

(71) Applicant: Willow Laboratories, Inc., Irvine, CA (US)

(72) Inventors: Gregory A. Olsen, Lake Forest, CA (US); Sai Kong Frank Lee, Irvine, CA (US); Hung The Vo, Fountain Valley, CA (US); Kevin Hughes Pauley, Lake Forest, CA (US)

(73) Assignee: WILLOW LABORATORIES, INC., Irvine, CA (US)

( * ) Notice: Subject to any disclaimer, the term of this patent is extended or adjusted under 35 U.S.C. 154(b) by 692 days.

(21) Appl. No.: 17/235,747

(22) Filed: Apr. 20, 2021

(65) Prior Publication Data

US 2021/0330228 A1    Oct. 28, 2021

Related U.S. Application Data

(60) Provisional application No. 63/013,718, filed on Apr. 22, 2020.

(51) Int. Cl.
*A61B 5/00* (2006.01)
*A61B 5/15* (2006.01)
*A61B 5/151* (2006.01)

(52) U.S. Cl.
CPC .... *A61B 5/15192* (2013.01); *A61B 5/150022* (2013.01); *A61B 5/1513* (2013.01); *A61B 2560/04* (2013.01)

(58) Field of Classification Search
CPC .......... A61B 5/15192; A61B 5/150022; A61B 5/1513; A61B 2560/04; A61B 5/150358;
(Continued)

(56) References Cited

U.S. PATENT DOCUMENTS 4,960,128 A   10/1990   Gordon et al.
4,964,408 A   10/1990   Hink et al.
(Continued)

FOREIGN PATENT DOCUMENTS

WO    WO 02/078533     10/2002
WO    WO 2021/216596   10/2021

OTHER PUBLICATIONS

US 2024/0016391 A1, 01/2024, Lapotko et al. (withdrawn)
(Continued)

*Primary Examiner* — May A Abouelela
(74) *Attorney, Agent, or Firm* — Knobbe, Martens, Olson & Bear, LLP

(57) ABSTRACT

A minimal action, invasive blood constituent device can streamline the process for the self-monitoring of blood-related tests by holding and facilitating the use of some or all of the tools for obtaining and testing a blood sample. The device can include a slider, that when pumped, causes the device to spring-load a lancet and eject a testing strip. The device can include a trigger that, when pressed, activates the lancet by unloading the spring. A strip-lancet apparatus can combine the roles of two disposable products—a testing strip and a lancing needle—into an apparatus that can be configured for piercing the testing site as well as receiving the blood sample. A testing strip apparatus can facilitate the use and/or disposal of testing strips. A lancet apparatus can facilitate the use and/or disposal of lancets.

10 Claims, 14 Drawing Sheets

(58) Field of Classification Search
CPC ........ A61B 5/150412; A61B 5/150748; A61B 5/157
See application file for complete search history.

(56) References Cited

U.S. PATENT DOCUMENTS

| | | | |
|---|---|---|---|
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |

(56) References Cited

U.S. PATENT DOCUMENTS

| | | |
|---|---|---|
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,892,185 B2 | 2/2011 | Freeman et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,204,834 B1 * | 12/2015 | DePaul ............ A61B 5/150175 |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,463,463 B2 | 10/2016 | He et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |

(56) References Cited

U.S. PATENT DOCUMENTS

| | | |
|---|---|---|
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |

(56) References Cited

U.S. PATENT DOCUMENTS

| | | |
|---|---|---|
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| 11,951,186 B2 | 4/2024 | Krishnamani et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0089861 A1 | 4/2005 | Allen |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0004522 A1* | 1/2010 | Varela ............ A61B 5/150503 600/347 |
| 2010/0030040 A1 | 2/2010 | Poeze et al. |
| 2010/0087754 A1* | 4/2010 | Rush ............ A61B 5/150862 600/583 |
| 2010/0099964 A1 | 4/2010 | O'Reilly et al. |
| 2010/0210970 A1* | 8/2010 | Horikawa ........ A61B 5/150793 600/583 |
| 2010/0222703 A1* | 9/2010 | Takashima ....... A61B 5/150358 600/583 |
| 2010/0234718 A1 | 9/2010 | Sampath et al. |
| 2010/0256526 A1* | 10/2010 | Harttig ............ A61B 5/150503 600/583 |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0178435 A1 | 7/2011 | Roe |
| 2011/0282173 A1* | 11/2011 | Fonduca .......... A61B 5/150022 600/365 |
| 2012/0123231 A1 | 5/2012 | O'Reilly |
| 2012/0165629 A1 | 6/2012 | Merritt et al. |
| 2012/0172760 A1* | 7/2012 | Roe ................. A61B 5/150167 600/583 |
| 2012/0209084 A1 | 8/2012 | Olsen et al. |
| 2012/0226117 A1 | 9/2012 | Lamego et al. |
| 2012/0271123 A1* | 10/2012 | Castle ............. A61B 5/150946 600/309 |
| 2012/0283524 A1 | 11/2012 | Kiani et al. |
| 2012/0330189 A1* | 12/2012 | Shaanan .......... G01N 33/48757 600/583 |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0085349 A1 | 4/2013 | Shaanan et al. |
| 2013/0096405 A1 | 4/2013 | Garfio |
| 2013/0172711 A1* | 7/2013 | Tamir ............. A61B 5/15142 600/365 |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0213935 A1* | 7/2014 | Hsu ................. A61B 5/14532 600/583 |
| 2014/0243635 A1* | 8/2014 | Arefieg ........... A61B 5/150854 600/365 |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2014/0364767 A1* | 12/2014 | Terashima ........ A61B 5/15111 600/583 |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0160186 A1* | 6/2015 | Garner-Richards .................... A61B 5/150503 221/270 |
| 2016/0196388 A1 | 7/2016 | Lamego |
| 2016/0367173 A1 | 12/2016 | Dalvi et al. |
| 2017/0000349 A1* | 1/2017 | Krief ............... A61B 5/15113 |
| 2017/0024748 A1 | 1/2017 | Haider |
| 2017/0035337 A1* | 2/2017 | Wilkinson ....... A61B 5/150786 |
| 2017/0143245 A1* | 5/2017 | Cohen ............. A61B 5/15113 |
| 2017/0173632 A1 | 6/2017 | Al-Ali |
| 2017/0251974 A1 | 9/2017 | Shreim et al. |
| 2018/0242926 A1 | 8/2018 | Muhsin et al. |
| 2018/0247712 A1 | 8/2018 | Muhsin et al. |
| 2018/0296148 A1* | 10/2018 | Gelfand .......... B01L 3/50273 |
| 2019/0117070 A1 | 4/2019 | Muhsin et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0054260 A1* | 2/2020 | Hatamian ........ A61B 5/150099 |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |

(56) References Cited

U.S. PATENT DOCUMENTS

| | | | |
|---|---|---|---|
| 2021/0113121 A1 | 4/2021 | Diab et al. | |
| 2021/0117525 A1 | 4/2021 | Kiani et al. | |
| 2021/0118581 A1 | 4/2021 | Kiani et al. | |
| 2021/0121582 A1 | 4/2021 | Krishnamani et al. | |
| 2021/0161465 A1 | 6/2021 | Barker et al. | |
| 2021/0186390 A1* | 6/2021 | Postle | A61B 5/157 |
| 2021/0196164 A1* | 7/2021 | Ivosevic | A61B 5/150137 |
| 2021/0236729 A1 | 8/2021 | Kiani et al. | |
| 2021/0256267 A1 | 8/2021 | Ranasinghe et al. | |
| 2021/0256835 A1 | 8/2021 | Ranasinghe et al. | |
| 2021/0275101 A1 | 9/2021 | Vo et al. | |
| 2021/0290060 A1 | 9/2021 | Ahmed | |
| 2021/0290072 A1 | 9/2021 | Forrest | |
| 2021/0290080 A1 | 9/2021 | Ahmed | |
| 2021/0290120 A1 | 9/2021 | Al-Ali | |
| 2021/0290177 A1 | 9/2021 | Novak, Jr. | |
| 2021/0290184 A1 | 9/2021 | Ahmed | |
| 2021/0296008 A1 | 9/2021 | Novak, Jr. | |
| 2021/0330228 A1 | 10/2021 | Olsen et al. | |
| 2021/0386382 A1 | 12/2021 | Olsen et al. | |
| 2021/0402110 A1 | 12/2021 | Pauley et al. | |
| 2022/0026355 A1 | 1/2022 | Normand et al. | |
| 2022/0039707 A1 | 2/2022 | Sharma et al. | |
| 2022/0053892 A1 | 2/2022 | Al-Ali et al. | |
| 2022/0071562 A1 | 3/2022 | Kiani | |
| 2022/0096603 A1 | 3/2022 | Kiani et al. | |
| 2022/0151521 A1 | 5/2022 | Krishnamani et al. | |
| 2022/0218244 A1 | 7/2022 | Kiani et al. | |
| 2022/0287574 A1 | 9/2022 | Telfort et al. | |
| 2022/0296161 A1 | 9/2022 | Al-Ali et al. | |
| 2022/0361819 A1 | 11/2022 | Al-Ali et al. | |
| 2022/0379059 A1 | 12/2022 | Yu et al. | |
| 2022/0392610 A1 | 12/2022 | Kiani et al. | |
| 2023/0028745 A1 | 1/2023 | Al-Ali | |
| 2023/0038389 A1 | 2/2023 | Vo | |
| 2023/0045647 A1 | 2/2023 | Vo | |
| 2023/0058052 A1 | 2/2023 | Al-Ali | |
| 2023/0058342 A1 | 2/2023 | Kiani | |
| 2023/0069789 A1 | 3/2023 | Koo et al. | |
| 2023/0087671 A1 | 3/2023 | Telfort et al. | |
| 2023/0110152 A1 | 4/2023 | Forrest et al. | |
| 2023/0111198 A1 | 4/2023 | Yu et al. | |
| 2023/0115397 A1 | 4/2023 | Vo et al. | |
| 2023/0116371 A1 | 4/2023 | Mills et al. | |
| 2023/0135297 A1 | 5/2023 | Kiani et al. | |
| 2023/0138098 A1 | 5/2023 | Telfort et al. | |
| 2023/0145155 A1 | 5/2023 | Krishnamani et al. | |
| 2023/0147750 A1 | 5/2023 | Barker et al. | |
| 2023/0210417 A1 | 7/2023 | Al-Ali et al. | |
| 2023/0222805 A1 | 7/2023 | Muhsin et al. | |
| 2023/0222887 A1 | 7/2023 | Muhsin et al. | |
| 2023/0226331 A1 | 7/2023 | Kiani et al. | |
| 2023/0284916 A1 | 9/2023 | Telfort | |
| 2023/0284943 A1 | 9/2023 | Scruggs et al. | |
| 2023/0301562 A1 | 9/2023 | Scruggs et al. | |
| 2023/0346993 A1 | 11/2023 | Kiani et al. | |
| 2023/0368221 A1 | 11/2023 | Haider | |
| 2023/0371893 A1 | 11/2023 | Al-Ali et al. | |
| 2023/0389837 A1 | 12/2023 | Krishnamani et al. | |
| 2024/0016418 A1 | 1/2024 | Devadoss et al. | |
| 2024/0016419 A1 | 1/2024 | Devadoss et al. | |
| 2024/0047061 A1 | 2/2024 | Al-Ali et al. | |
| 2024/0049310 A1 | 2/2024 | Al-Ali et al. | |
| 2024/0049986 A1 | 2/2024 | Al-Ali et al. | |
| 2024/0081656 A1 | 3/2024 | DeJong et al. | |
| 2024/0122486 A1 | 4/2024 | Kiani | |

OTHER PUBLICATIONS

International Search Report and Written Opinion received in PCT Application No. PCT/US2021/028224, as mailed Aug. 6, 2021 in 11 pages.

* cited by examiner

SELF-CONTAINED MINIMAL ACTION INVASIVE BLOOD CONSTITUENT SYSTEM

CROSS-REFERENCE TO RELATED APPLICATIONS

This application claims the benefit of priority under 35 U.S.C. § 119(e) to U.S. Provisional Application No. 63/013,718, filed on Apr. 22, 2020, entitled "SELF-CONTAINED MINIMAL ACTION INVASIVE BLOOD CONSTITUENT SYSTEM," which is hereby incorporated by reference in its entirety.

TECHNICAL FIELD

The present disclosure relates generally to the field of physiological monitoring. More specifically, the present disclosure relates to systems, methods, and/or apparatuses for taking blood analyte measurements.

BACKGROUND

Monitoring of blood glucose (blood sugar) concentration levels has long been critical to the treatment of diabetes in humans. Current blood glucose monitoring generally involves a chemical reaction between blood serum and a test strip, requiring an extraction of blood via a lancet or pinprick. Small handheld monitors have been developed to enable a patient to perform this procedure anywhere, at any time. But the procedure—specifically the blood extraction and the use and disposition of test strips—can often require numerous pieces of equipment and a number of tedious steps.

SUMMARY

A blood constituent device can include a trigger, a testing strip, a lancet, and a slider. A predefined movement of the slider can cause the device to load the lancet. A predefined movement of the slider can cause the device to present the testing strip. Activation of the trigger after loading the lancet can cause the device to activate the lancet. Activation of the lancet can cause the lancet to prick a measurement site of a user.

The blood constituent device of the preceding paragraph and/or any of the apparatuses, systems, or devices disclosed herein can include one or more of the following features. The predefined movement can include sliding the slider in a first direction and/or sliding the slider in a second direction. Sliding the slider in the first direction can cause the device to load the lancet. Sliding the slider in the second direction can cause the device to present the testing strip. The device can include a lancing spring. Loading the lancet can include compressing the lancing spring, wherein activation of the lancet can include decompressing the lancing spring. The device can include a testing strip cartridge that can include a plurality of stacked testing strips. The plurality of stacked testing strips can include the testing strip. The device can include a strip guiding rod. A predefined movement of the slider can cause the strip guiding rod to move the testing strip from the plurality of stacked testing strips and present the testing strip.

The blood constituent device of any of the preceding paragraphs and/or any of the apparatuses, systems, or devices disclosed herein can include one or more of the following features. The device can include a testing strip disposal bin configured to store testing strips. A predefined movement of the slider can cause the device to add a used testing strip to the testing strip disposal bin. The device can include a lancet cartridge that can include a plurality of lancets. The plurality of lancets can include the lancet. A predefined movement of the slider can cause the device to select the lancet from the lancet cartridge and load the lancet. The device can include a lancet disposal bin configured to store lancets. A predefined movement of the slider can cause the device to add a used lancet to the lancet disposal bin. The testing strip disposal bin can be the same container as the lancet disposal bin. A user can place a blood sample on the testing strip. The device can include a glucometer configured to obtain data from the blood sample on the testing strip.

A method of using an invasive blood constituent device that can include sliding a slider of an invasive blood constituent device according to a predefined movement. Sliding the slider in the predefined movement can cause the device to load the lancet and/or present the testing strip. The method can include, after loading the lancet, activating a trigger of the invasive blood constituent device. Activation of the trigger after loading the lancet can cause the device to activate the lancet. Activation of the lancet can cause the lancet to prick a measurement site of a user.

The method of any of the preceding paragraphs can include one or more of the following steps or features. The predefined movement can include sliding the slider in a first direction and/or sliding the slider in a second direction. The invasive blood constituent device that can include one or more of the features of the device of any of the previous claims.

A testing strip apparatus can include a trigger, a testing strip cartridge that can include a plurality of stacked testing strips, and a strip guiding rod. Activation of the trigger can cause the strip guiding rod to move a testing strip from the plurality of stacked testing strips and present the testing strip to a user.

The testing strip apparatus of the preceding paragraph and/or any of the apparatuses, systems, or devices disclosed herein can include one or more of the following features. The testing strip apparatus can include a testing strip disposal bin configured to store testing strips for later disposal. Activation of the trigger can cause a previously used testing strip to move into the testing strip disposal bin.

A lancet apparatus can include a trigger and a lancet cartridge that can include a plurality of lancets. Activation of the trigger can cause the device to select a lancet from the plurality of lancets and load the selected lancet.

The lancet apparatus of the preceding paragraph and/or any of the apparatuses, systems, or devices disclosed herein can include one or more of the following features. The lancet apparatus can include a lancet disposal bin configured to store lancets for later disposal. Activation of the trigger can cause a previously used lancet to move into the lancet disposal bin. Activation of the trigger can cause the selected lancet to project from the lancet apparatus to prick a measurement site of a user.

A strip-lancet apparatus that can include a first layer that can include a testing strip for accepting a blood sample, and a second layer that can include a lancing needle for pricking skin at a measurement site.

The strip-lancet apparatus of the preceding paragraph and/or any of the apparatuses, systems, or devices disclosed herein can include one or more of the following features. The first layer can be configured to move relative to the second layer. In a first configuration the lancing needle can be exposed to a user. In a second configuration the lancing needle can be isolated from the user. In a first configuration the first layer can be offset from the second layer. In a second configuration the first layer can be aligned with the second layer. To transition from the first configuration to the second configuration, the first layer can be shifted relative to the second layer. The first layer can be retractable relative to the second layer. The second layer can be retractable relative to the first layer. The strip-lancet apparatus can transition from the second configuration to the first configuration responsive to force applied on the first layer by a launching mechanism. The launching mechanism can be a spring. The strip-lancet apparatus can transition from the first configuration to the second configuration responsive to force applied on the first layer by a recoil mechanism. The recoil mechanism can be a spring. A direction of the force applied on the first layer by the launching mechanism can be opposite to a direction of the force applied on the first layer by the recoil mechanism. The strip-lancet apparatus can be rectangular.

A strip-lancet apparatus that can include a lancing needle for pricking skin at a measurement site and a testing strip for accepting a blood sample. In a first configuration the lancing needle can protrude from an edge of the strip-lancet apparatus. In a second configuration the strip-lancet apparatus can be recoiled into the strip-lancet apparatus.

For purposes of summarizing the disclosure, certain aspects, advantages, and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

FIGS. 1B-1 and 1B-2 (individually or collectively referred to as FIG. 1B) illustrate a top perspective view of the handheld invasive blood constituent device of FIG. 1A.

FIGS. 1D-1 and 1D-2 (individually or collectively referred to as FIG. 1D) illustrate example interview components of the handheld invasive blood constituent device of FIG. 1A.

FIGS. 2A-1 and 2A-2 (individually or collectively referred to as FIG. 2A), FIGS. 2B-1, 2B-2 (individually or collectively referred to as FIG. 2B), FIGS. 2C-1 and 2C-2 (individually or collectively referred to as FIG. 2C), and FIGS. 2D-1 and 2D-2 (individually or collectively referred to as FIG. 2D) illustrate cross-sectional views of a transitional sequence of internal physical mechanical motions of an example handheld invasive blood constituent device.

Figures 1, 1A:
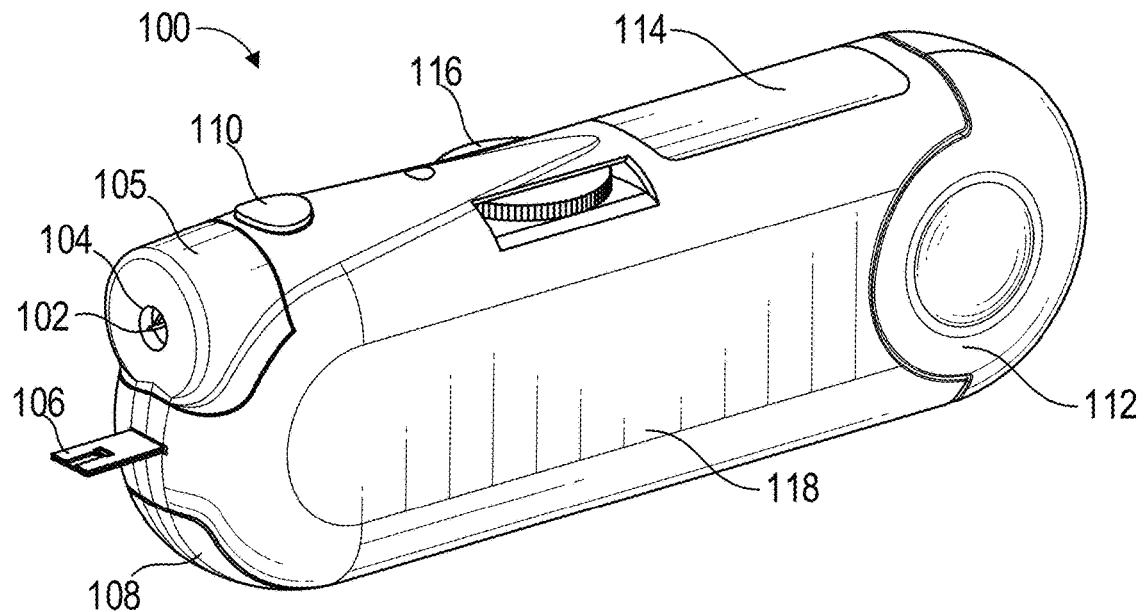
FIGS. 1A-1 and 1A-2 (individually or collectively referred to as FIG. 1A) illustrate a side perspective view of an example handheld invasive blood constituent device.
Figures 1, 1A, 2:
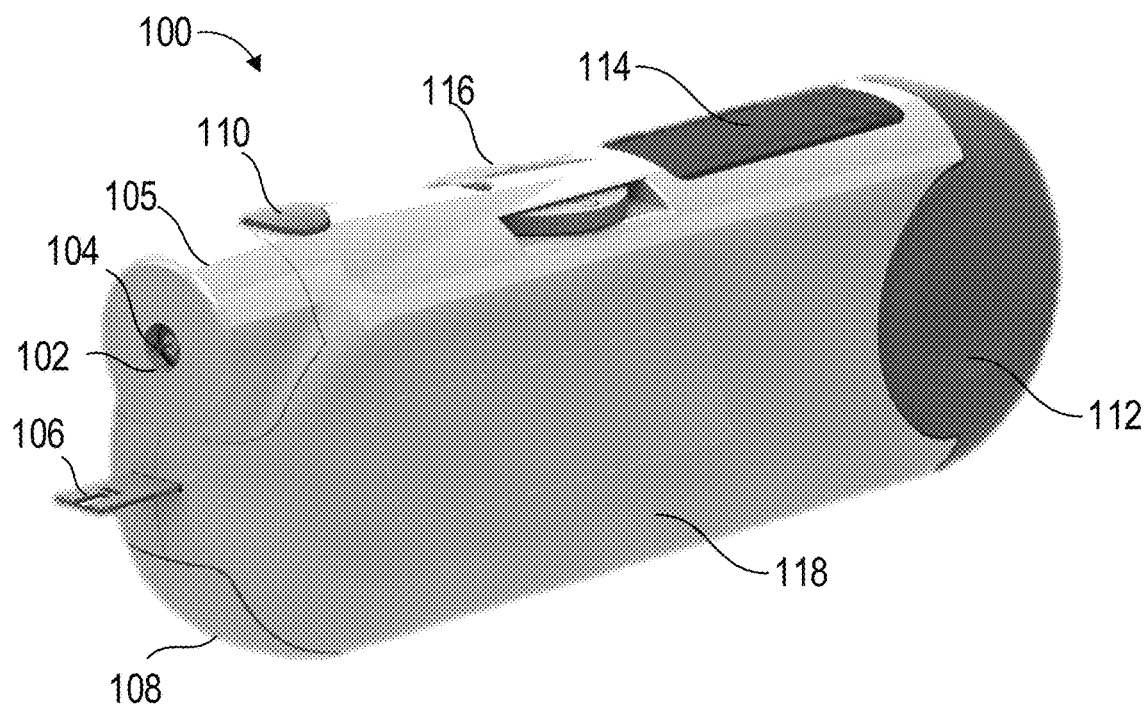

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

The present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, embodiments disclosed herein can include several novel features, no single one of which is solely responsible for its desirable attributes or which is essential to practicing the systems, devices, and methods disclosed herein.

INTRODUCTION

And individuals with Type 1 or Type 2 diabetes and those that perform Glucose monitoring are often tasked with self monitoring of blood glucose (or SMBG) using a blood analyte monitor, sometimes multiple times per day. The traditional process for SMBG, which includes opening a carrying case, loading a lancet into a lancing device, opening a testing strip container to obtain a testing strip, loading the testing strip into a blood constituent meter, preparing the test site, pricking the testing site, placing a blood sample on the testing strip, repeating one or more of the steps if an error occurs, discarding the used lancet, and discarding the used testing strip, can be tedious, time consuming, and far from discrete. Moreover, many self-monitors feel embarrassed by the SMBG process, as they are often bothered with explaining to others why they test and what type of diabetes they have. These and other factors have led to a low level of compliance and a strong need for added convenience, simplicity, and discreetness.

Disclosed herein is a minimal action, invasive blood constituent device that can streamline the process for the self-monitoring of blood-related tests. The device can be a handheld or pocket-able apparatus that holds and facilitates the use of some or all of the tools for obtaining and testing a blood sample. For example, the device can hold a set of lancing needles and/or a set of testing strips and can include internal mechanisms for facilitating the user's use of those items. For instance, in some cases, a user can quickly, efficiently, and discreetly obtain a measurement by simply pumping a handle of the device to load a lancing needle and/or testing strip, pressing a button to launch the lancing needle (and cause the finger prick), and swiping the finger on a testing strip.

Users of SMBG systems often require numerous disposable components, such as testing strips and lancets, to facilitate the drawing of whole blood and collecting a sample. These components are often handled individually by users, potentially multiple times per day, before being disposed of. In practice, disposing of the components, particularly the lancets, can pose a safety hazard due at least in part to the potential for inadvertent pricks.

Disclosed herein is strip-lancet apparatus that can address one or more of these or other challenges. As described herein, a strip-lancet apparatus can combine the roles of two disposable products—a testing strip and a lancing needle—into an apparatus that can be configured for piercing the testing site as well as receiving the blood sample. In some cases, the strip-lancet apparatus can be configured such that a user rarely handles it when the lancing needle is exposed. For example, the strip-lancet apparatus can include a retractable lancet feature that ensures the lancing needle is isolated from the user, except for a limited amount of time during which it is used to prick the measurement site. In this way, the strip-lancet apparatus can improve the user's safety.

Example Blood Constituent Device

A minimal action, invasive blood constituent device can streamline the process for the self-monitoring of blood-related tests. The device can be a handheld or pocket-able apparatus that holds and facilitates the use of some or all of the tools for obtaining and testing a blood sample. Thus, the device can provide added convenience, simplicity, and discreetness to blood-related testing, such as testing relating to blood analyte(s) (such as blood glucose or cholesterol), glucotype, Mononucleosis, Epstein-Barr Virus, genetic testing, IgG antibodies for food sensitivity, cancer biomarkers, the like, or a combination thereof.

Figures 1, 1B:
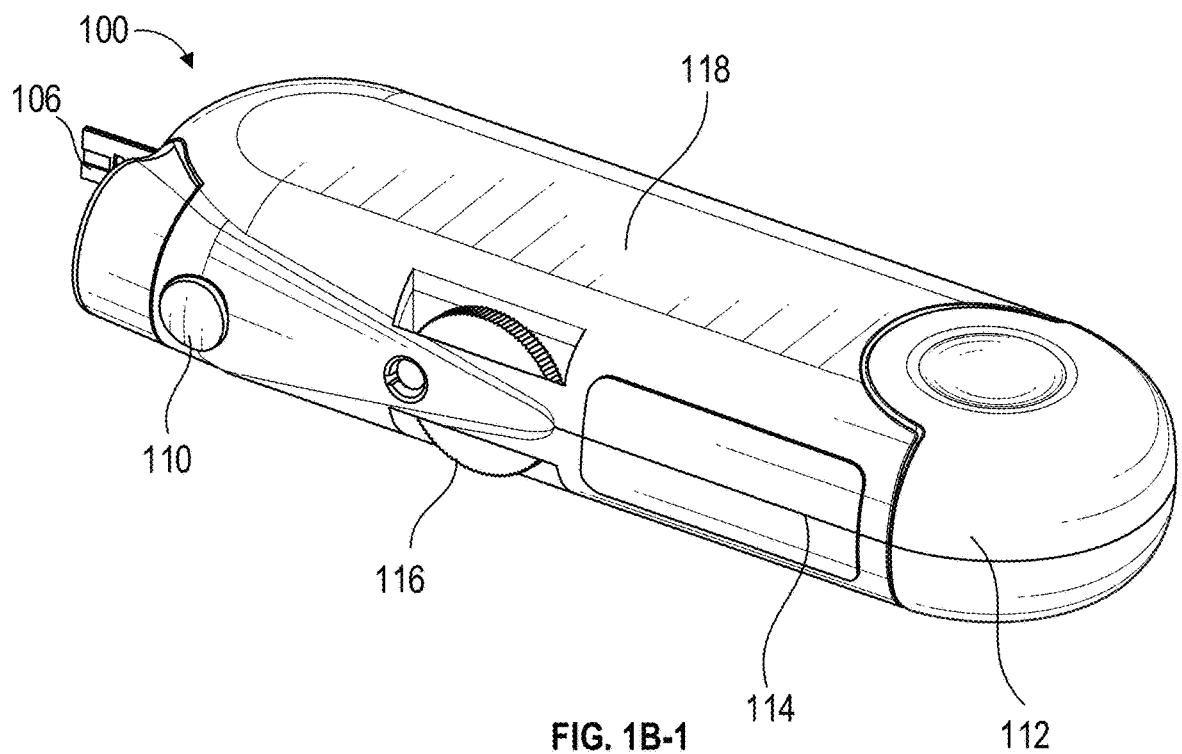
Figures 1, 1B, 2:
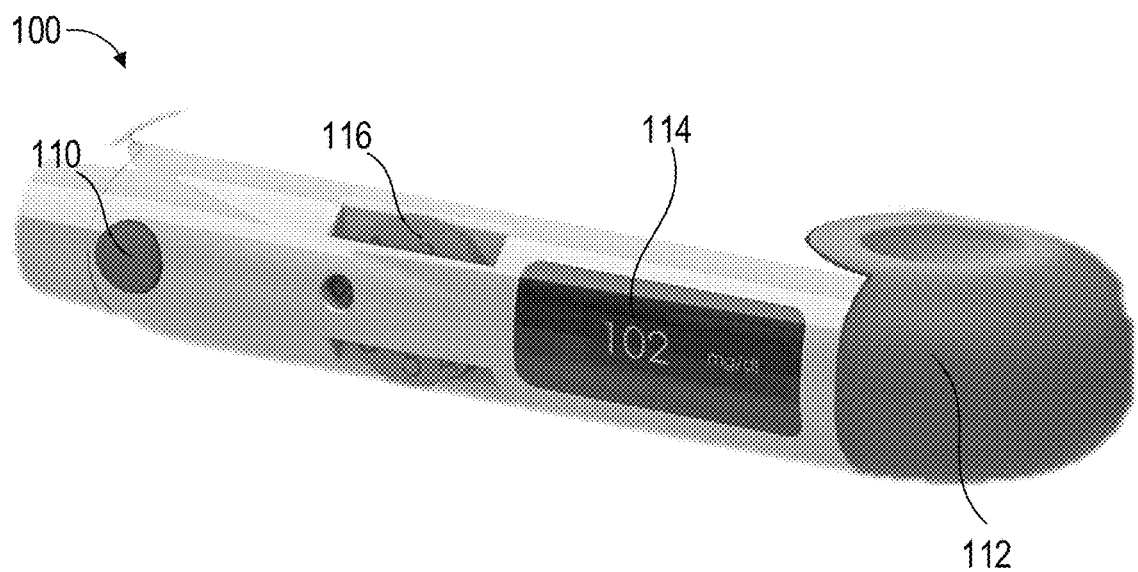
Figure 1C:
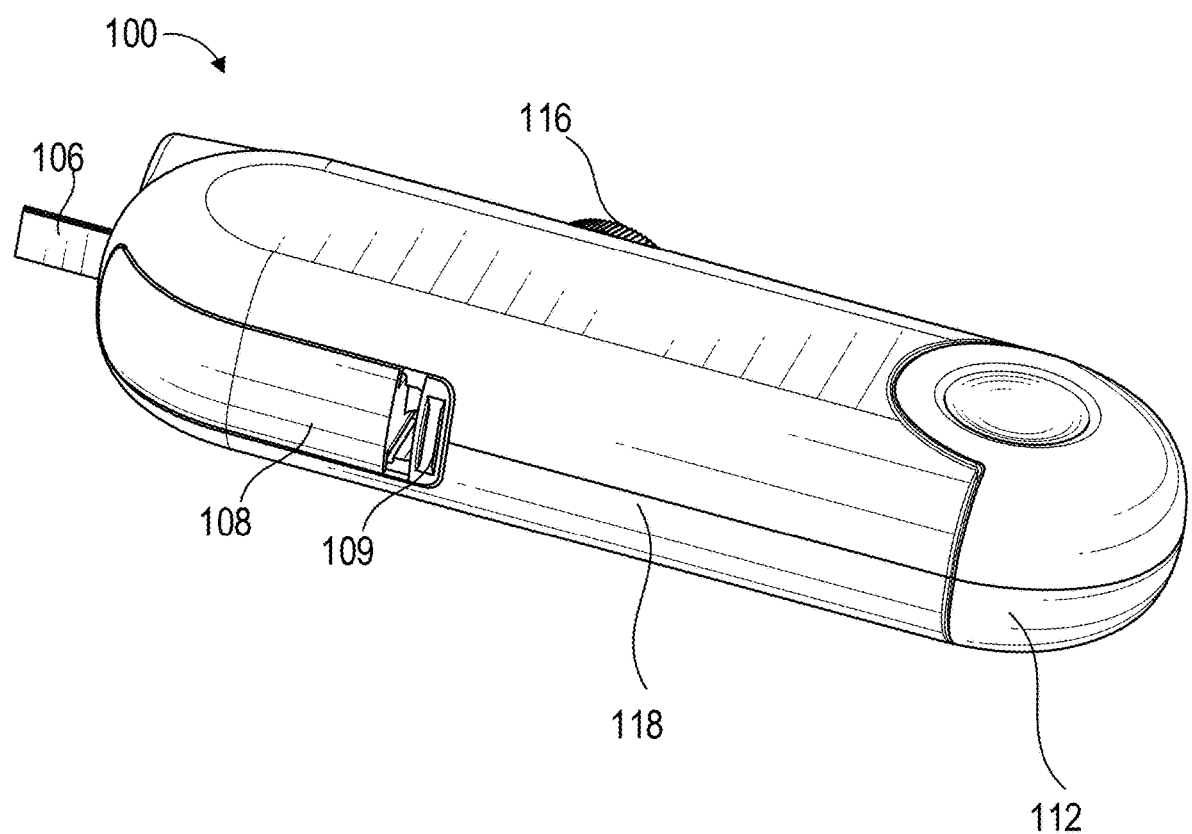
FIG. 1C illustrates a bottom perspective view of the handheld invasive blood constituent device of FIG. 1A.
Figures 1, 1D:
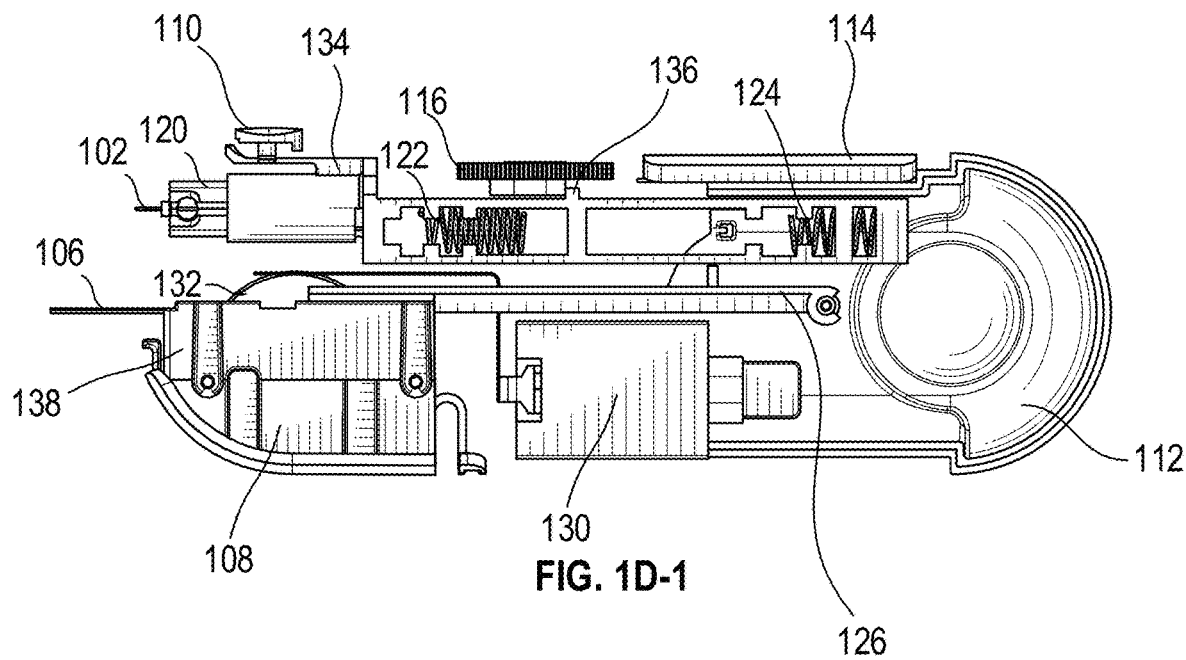
Figures 1, 1D, 2:
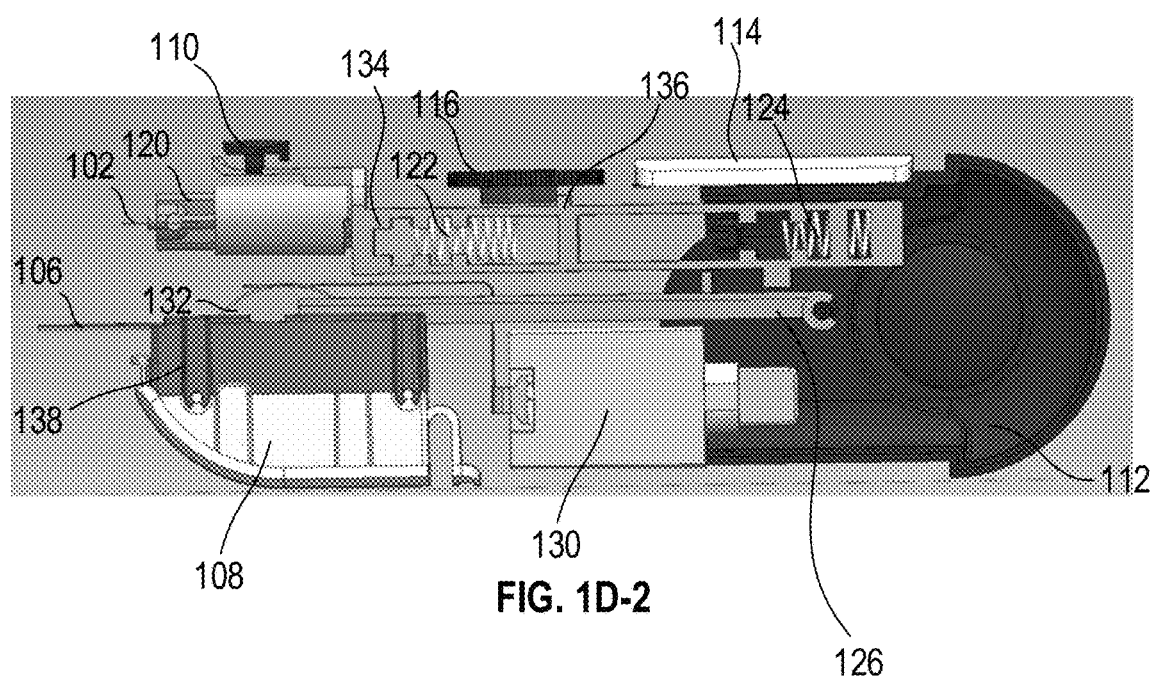

FIGS. 1A-1C illustrate perspective views, and FIG. 1D illustrates an exploded view, of an example invasive blood constituent device 100. As illustrated, the device 100 can be a handheld or pocket-able apparatus with a sleek design and small footprint. The device 100 can include a lancet 102, a finger alignment wall 104, a testing strip 106, an entry door 108 for a testing strip cartridge 138, a trigger 110, a slider 112, a display 114, a dial wheel 116, and a base portion 118. Further, as shown in FIG. 1D, the device 100 can include a lancet holder 120, one or more lancing springs 122, 124, a lancing frame 134, a strip guiding rod 126, a testing strip cartridge 138, a testing strip reader 130, and a power source 132. However, the device 100 can include fewer, more, or additional components.

In this implementation, the general controls of the device 100 include the slider 112 and the trigger 110. The slider 112 is configured for longitudinal movement. For instance, the user can pull or slide the slider 112 away from the base portion 118 in one motion, and then push or slide the slider 112 back towards the base portion 118 in another motion. These two motions (sometimes collectively referred to as "pumping" the slider 112 or "loading" the device 100) can, among other things, compress one or more of the lancing springs 122, 124 to spring-load the lancet 102. Pumping the slider 112 can also reveal the testing strip 106. In some cases, movement of the slider 112 can be locked for each transportation and/or safety concerns.

Once the device 100 is loaded, the user can place her finger against or proximate to the finger alignment wall 104 and activate the lancet 102. The way(s) in which the lancet 102 can be activated can vary across embodiments. For instance, in the illustrated implementation, the lancet 102 is activated by pressing the trigger 110 while the device 100 is loaded. When the trigger 110 is pressed down, the downward force on the trigger 110 causes the button to exert a downward force on the lancing frame 134, which displaces the lancing frame 134 in a downward direction. When the lancing frame 134 is displaced by a threshold amount, a stopper 136 on the lancing frame 134 that is held by the wheel 116 is released. The release of the stopper 136 causes the springs 122, 124 to unload, causing the lancing frame 134 and the lancet 102 to launch in the direction of the spring force (e.g., toward the finger alignment wall 104). Activating the lancet 102 in this way causes the lancing needle of the lancet 102 to move through a hole in the finger alignment wall 104 and prick the user's finger.

As another example, the lancet 102 can be activated by a motion sensing device. For instance, the device 100 can include a motion sensing device that detects if and/or when a user places her finger against or sufficiently proximate to the finger alignment wall 104, and can activate the lancet 102 based on such detection. As another example, the launching of the lancet 102 can be voice- or pressure-activated. As another example, the trigger 110 can be implemented in software and/or can be configured to activate the lancet 102 according to a predefined schedule.

Figures 1, 2A:
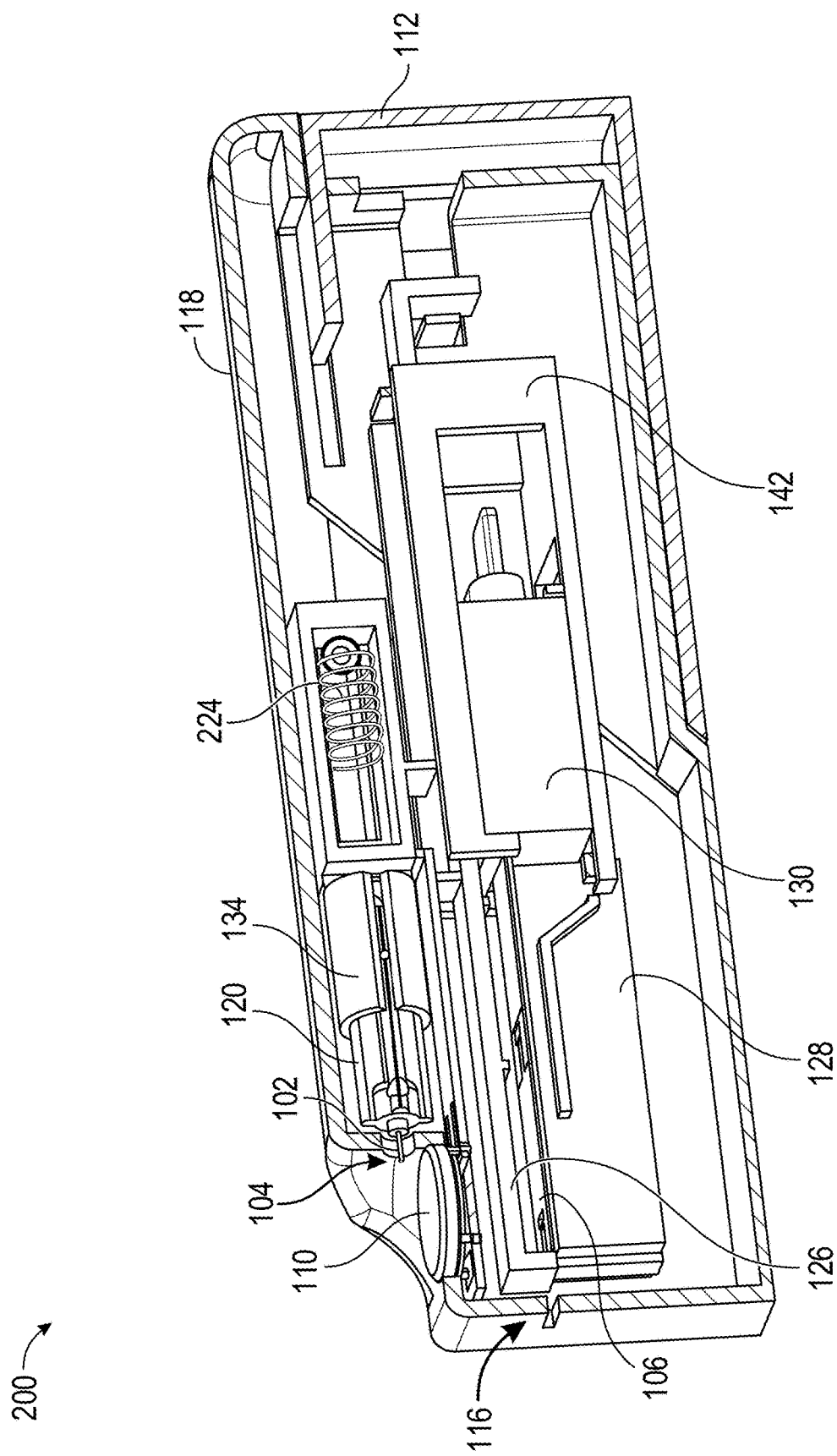
Figures 2, 2A:
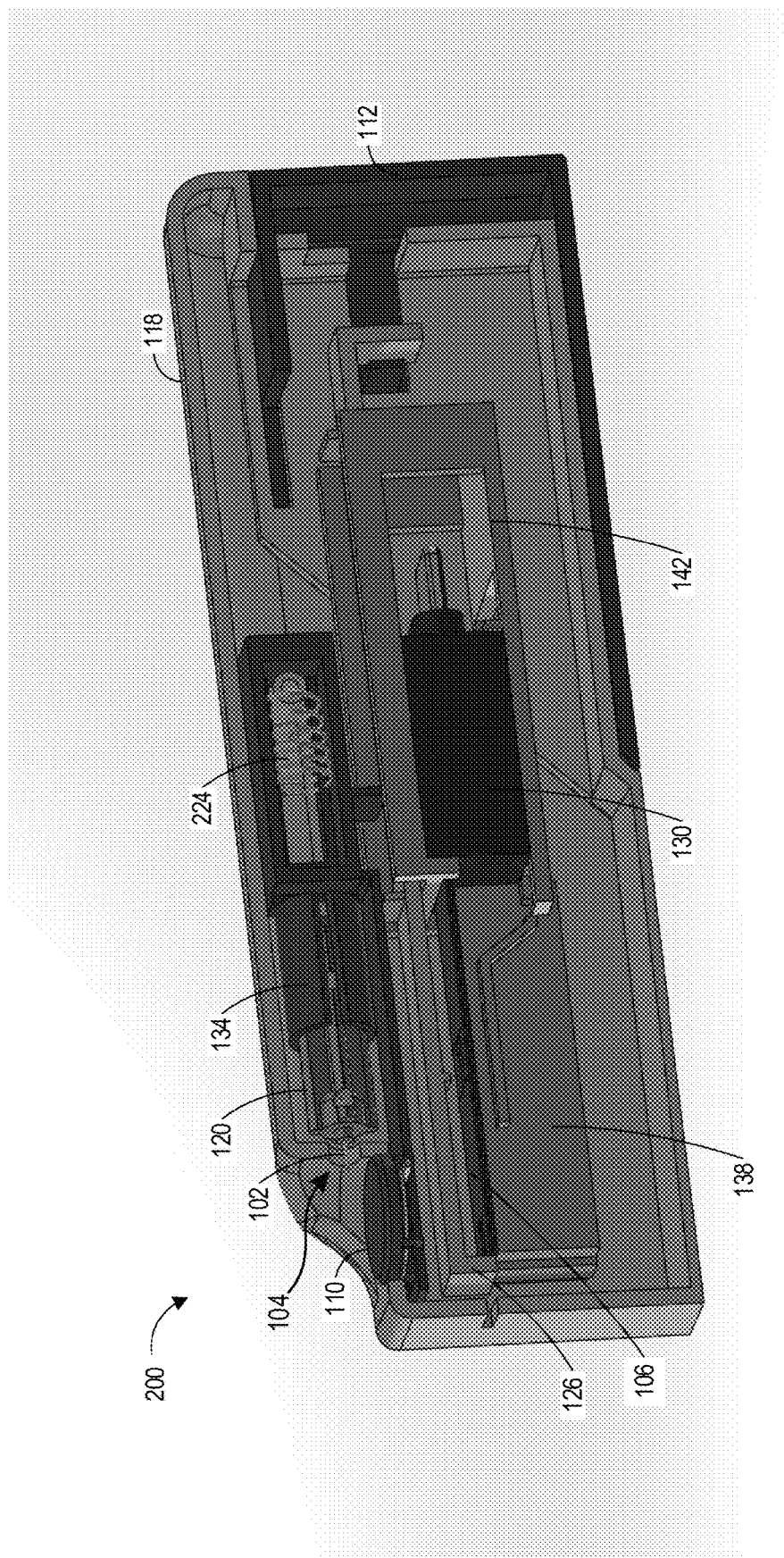

Although the lancet 102 and the trigger 110 are depicted as being located in separate regions on the device 100, in some cases, the lancet 102 and the trigger 110 may reside in proximate or overlapping regions of the device 100. For example, the lancet 102 can be integrated or part of the trigger 110, can be proximate to the trigger 110, or can be configured to launch through a hole in the trigger 110. In some such cases, the user can press or active the trigger 110 with her finger and the lancet 102 can prick that same finger. In some cases, for example as illustrated in the device of FIG. 2A, the pricking of the finger by the lancet 102 can occur as part of the same motion as the pressing or activating of the trigger 110 by the user. Furthermore, in some cases, the device 100 does not include a trigger 110.

The lancet 102 may remain retracted, or unloaded, within the device 100 until activation. For instance, the lancet 102 can be is temporarily activated before returning to its retracted, or deactivated, state. For example, activating the lancet 102 can cause the lancet 102 to launch from the device 100 to a particular depth beyond the device housing 118 or at a particular launching force. The lancet 102 can remain activated, protruding from the device 100, for a short period of time, such as a time just long enough to prick the finger, before returning to its retracted, deactivated position. In this way, the lancet 102 can remain generally inaccessible to a user, which can reduce the risk of inadvertent pricks.

The launching depth or launching force of lancet 102 can be fixed or controllable. For example, in the illustrated example, the device 100 includes a dial wheel 116, which can be rotated to adjust the launching depth or launching force of lancet 102, for example by adjusting the compression of one or more of the lancing springs 122, 124. However, it will be understood that the launching depth or launching force of lancet 102 can adjusted in a variety of ways, which can vary based on the embodiment. For example, in some cases, the launching depth or launching force of lancet 102 can be based at least in part on the distance over which the user pulls back on the slider 112. As another example, the launching depth or launching force of lancet 102 can be based at least in part on a force applied to the trigger 110. As another example, the launching depth or launching force of lancet 102 can be controllable and/or configurable by a processor, or can be based on a size of the lancet 102 itself.

Once blood is present, the user can move her finger a small distance to place a blood drop on to the testing strip 106.

The testing strip cartridge 138 can be configured to hold a set of testing strips 106, such as a single testing strip 106 or a plurality of stacked testing strips 106. For example, the testing strip cartridge 138 can hold several days' supply of testing strips. When the testing strip cartridge 138 becomes empty or low, the testing strip cartridge 138 can be refilled and/or replaced. For example, a user can squeeze the release button 109 on the entry door 108 to open the entry door 108 and remove, replace, and/or refill the testing strip cartridge 138. Additionally or alternatively, testing strip cartridge 138 can hold a set of strip-lancet apparatuses, as described herein. In some cases, the device 100 can eject a used testing strip 106 after it is used. For example, a used testing strip 106 can be ejected in response to the user performing a small or normal pump of the slider 112. In some cases, the device 100 compiles used testing strips internally, for example in an internal bin to be emptied by the user. In some cases, a blank test strip comes out last, which may indicate to the user that the internal bin is empty of testing strips or needs replenishing or replacement. In some cases, the display 114 can display a prompt telling the user that the cartridge is empty.

The device 100 can be configured to replace the lancet 102 after use. The lancet 102 can be replaced automatically by the device 100, or as a result of one or more actions performed by the user on the user device 100. For example, in some cases, pumping the slider 112 can remove a currently-loaded lancet 102 and can load a new lancet 102. For example, the device 100 can include another cartridge (not shown) that stores replacement and/or used lancets. In some cases, the device 100 can eject a used lancet 102 after it is used. For example, a used lancet 102 can be ejected in response to the user performing a small or normal pump of the slider 112. In some cases, the device 100 compiles used lancets 102 internally, for example in an internal bin. In some examples, the internal bin may be configured to be emptied of used lancets 102 by the user.

The display 114 can be configured to display content relating to the user, one or more measurements, or the like. For example, the display 114 can be configured to provide feedback regarding whether a correct amount of blood was placed on testing strip 106, or can display blood values, historical trends, glucotypes, etc.

The device 100 can include a processor for processing data, communicating with the testing strip reader 130, or controlling the display 114. In some cases, the device 100 may be configured to communicate with a mobile device (e.g., patient monitor, mobile phone, laptop, wearable device, etc.) For example, the device 100 may be configured with a wireless connection protocol, such as Bluetooth or a cellular connection. In some cases, the processor can be configured to count the remaining testing strips 106. For example, an electric contact can be tripped when the strip door reaches a minimum strips position. In some cases, the processor can be configured to count a number of times the slider 112 has been pumped, determine a number of glucose measurements made.

Although illustrated as a handheld device, the device 100 can be of various shapes and/or sizes. For example, in some cases, the device 100 could be implemented as a wearable device, such as a watch, watch band, bracelet, anklet, ring, or other jewelry.

In some cases, the device 100 can be configured to provide treatment or medicine to a user. For example, in some cases, the device 100 includes an insulin treatment feature, which allows a user to inject herself with insulin. For example, the injection of insulin could be performed in a similar manner to the activation of the lancet, as described herein.

In some cases, the front cap 105 of the device 100 can be removed and replaced with a magnetic alignment. Additionally or alternatively, the device 100 may use magnets on the entry door 108 for the testing strip cartridge 138 and for testing strip cartridge 138 placement. In some cases, the front cap 105 can be removed so that the user can pull out and/or replace a lancet 102.

In some cases, the device 100 may not include a lancet. For example, the device 100 can be configured to facilitate the storage and/or distribution of testing strips. In some such cases, the device 100 can be referred to as a testing strip apparatus. As an example, the device 100 can include a trigger 110. Further, the device 100 can include a testing strip cartridge 138 that includes a plurality of stacked testing strips. The device 100 can include a strip guiding rod 126. In some cases, activation of the trigger 110 causes the strip guiding rod 126 to move a testing strip 106 from the plurality of stacked testing strips and present the testing strip to a user. The device 100 can include a testing strip disposal bin (not pictured) configured to store testing strips for later disposal. In some cases, activation of the trigger 110 causes a previously used testing strip to move into the testing strip disposal bin.

In some cases, the device 100 may not include a testing strip. For example, the device 100 can be configured to facilitate the storage and/or distribution of lancets. In some such cases, the device 100 can be referred to as a lancet apparatus. As an example, the device 100 can include a trigger 110. Further, the device 100 can include a lancet cartridge (not pictured) that includes a plurality of lancets. In some cases, activation of the trigger 110 causes the device to select a lancet from the plurality of lancets and load the selected lancet. As described herein, wherein activation of the trigger can cause the selected lancet to project from the device 100 to prick a measurement site of a user. The device 100 can include a lancet disposal bin (not pictured) configured to store lancets for later disposal. In some cases, activation of the trigger 110 causes a previously used lancet to move into the lancet disposal bin. The lancet disposal bin can be separate from the lancet cartridge, such that the lancet cartridge includes unused lancets and the lancet disposal bin includes used or previously-loaded lancets.

FIGS. 2A-2D illustrate cross-sectional views of a transitional sequence of internal physical mechanical motions of an example invasive blood constituent device 200, which can be an embodiment of the handheld invasive blood constituent device 100 of FIG. 1A. As illustrated, the device 200 can include a lancet 102, a finger alignment wall 104, a testing strip 106, a testing strip cartridge 138, a trigger 110, a slider 112, a base portion 118, a lancet holder 120, a lancing frame 134, a lancing spring 224, a strip guiding rod 126, a testing strip reader 130, and a strip reader frame 142. However, the device 100 can include fewer, more, or additional components.

FIG. 2A illustrates a cross-sectional view of the device 200 in an unloaded or beginning state. In this state, the lancing spring 224 is unloaded such that pressing the trigger 110 will not cause the lancet 102 to activate. Furthermore, no testing strip 106 is revealed. The device 200 may be in an unloaded state prior to the first use of the device 100, or may be in an unloaded state responsive to a usage of the device 100 (e.g., activation of the lancet 102).

Figures 1, 2B:
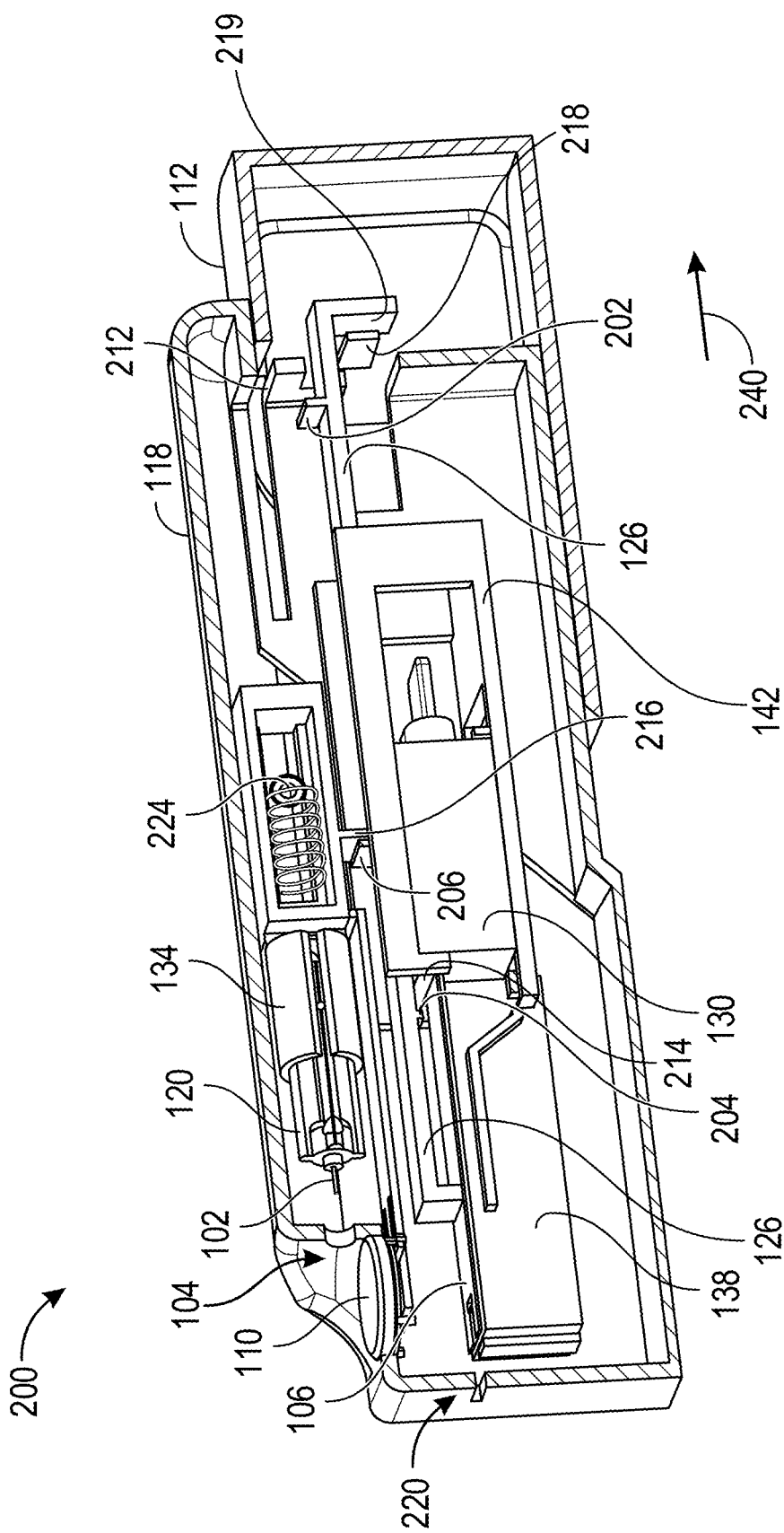
Figures 2, 2B:
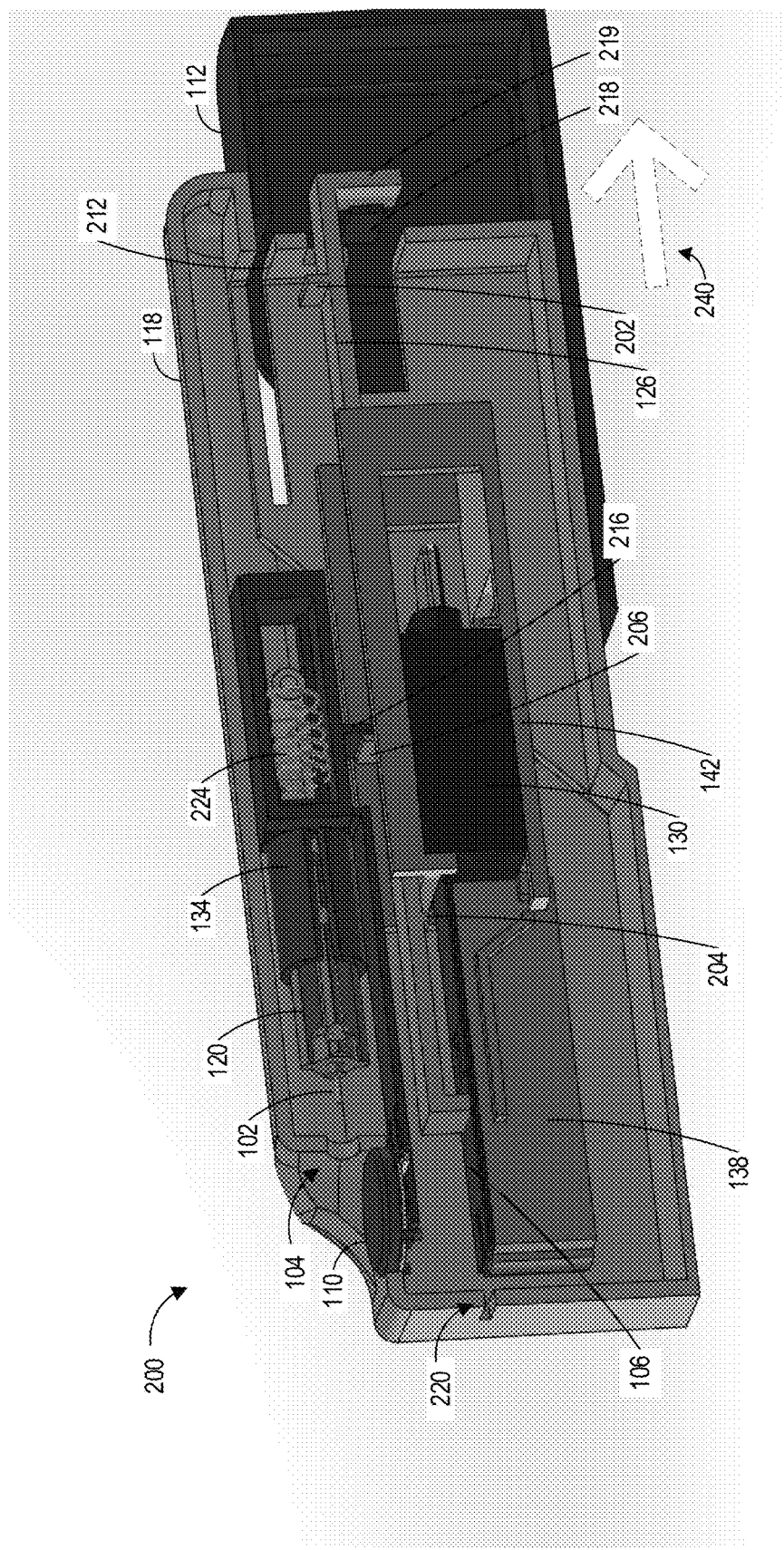

As shown in FIG. 2B, as the user begins to shift the slider 112 in the first direction 240 relative to the base portion 118 of the device 200. In this implementation, the slider 112 includes a projection 218 that catches the end 219 of the strip guiding rod 222 as the slider 112 is shifted, thereby causing the strip guiding rod 222 to shift as well.

Figures 1, 2C:
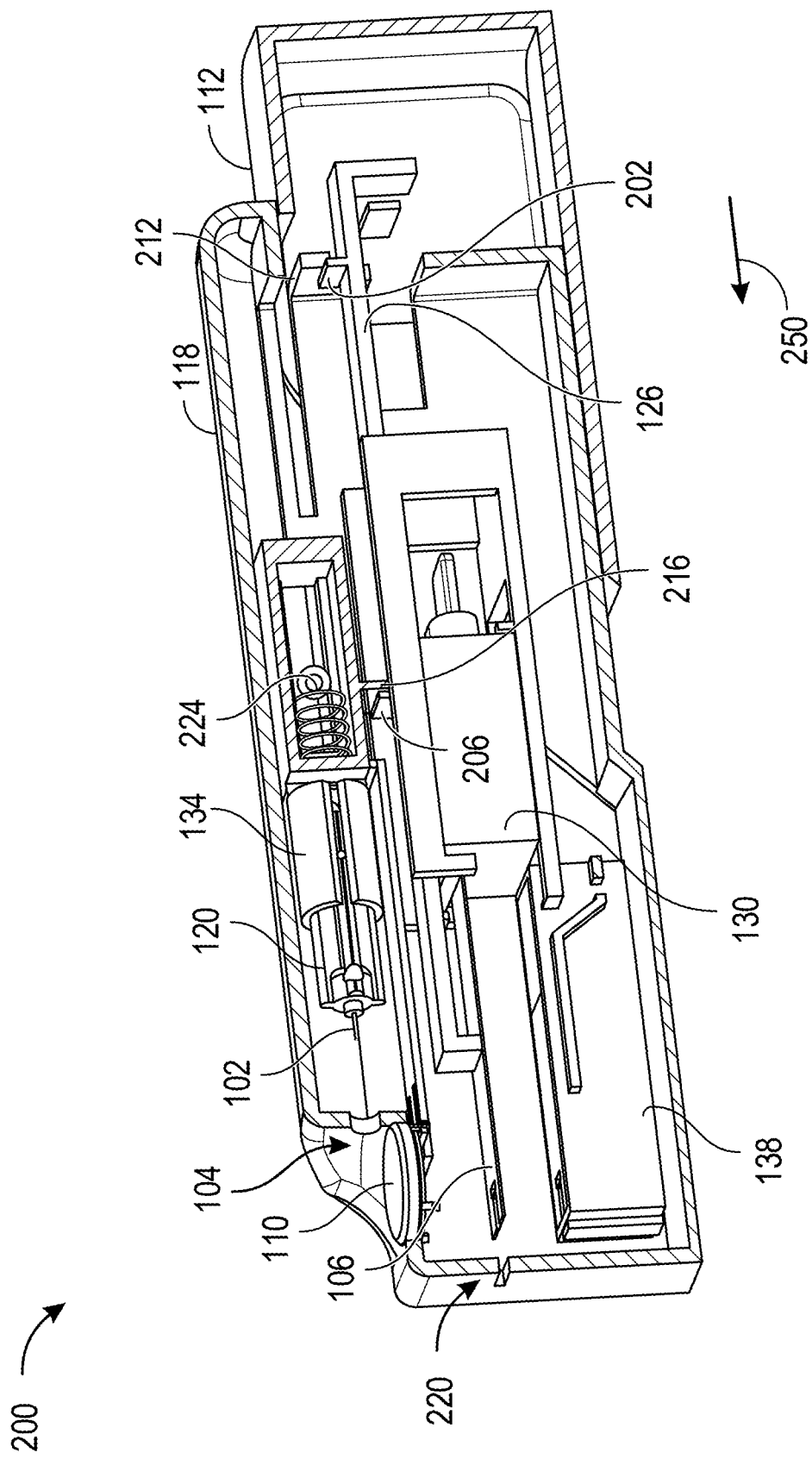
Figures 2, 2C:
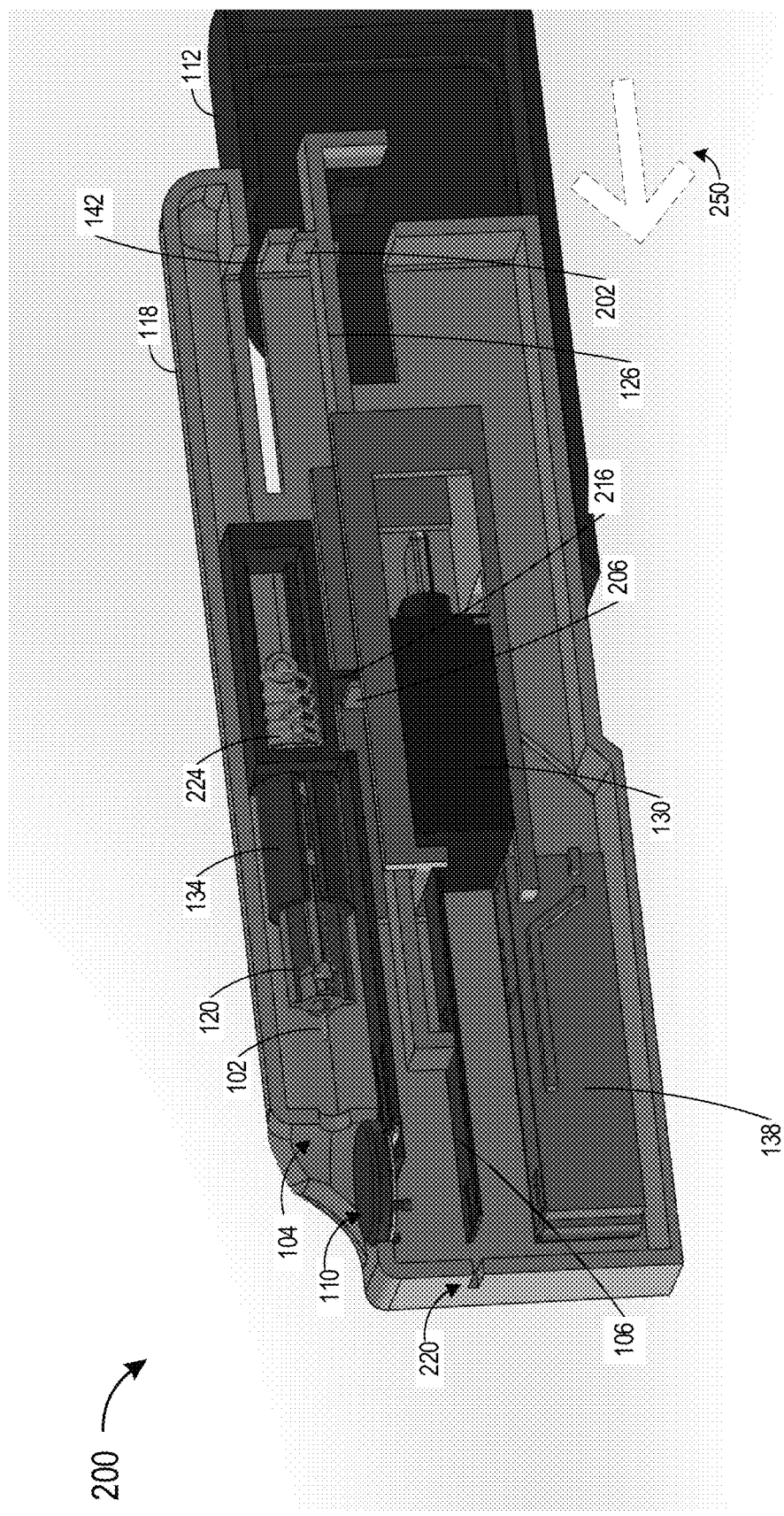

As shown in FIG. 2C, as the user continues to pull the slider 112 in the first direction 240, the slider 112 and the strip guiding rod 222 continue to pull back until the protrusion 202 hits the end stop 212 base portion 118, thereby limiting the range of motion of the strip guiding rod 222 and the slider 112. Furthermore, as the strip guiding rod 222 is moved in the first direction 240, the protrusion 206 of the strip guiding rod 222 catches the protrusion 216 of the lancing frame 134, causing the lancing frame 134 to be displaced in the direction of the pull force and further causing the lancing spring 224 to become compressed, thereby loading the lancet 102. Furthermore, as the strip guiding rod 222 is moved in the first direction 240, the protrusion 204 of the strip guiding rod 222 catches the protrusion 214 of the strip reader frame 142.

Figures 1, 2D:
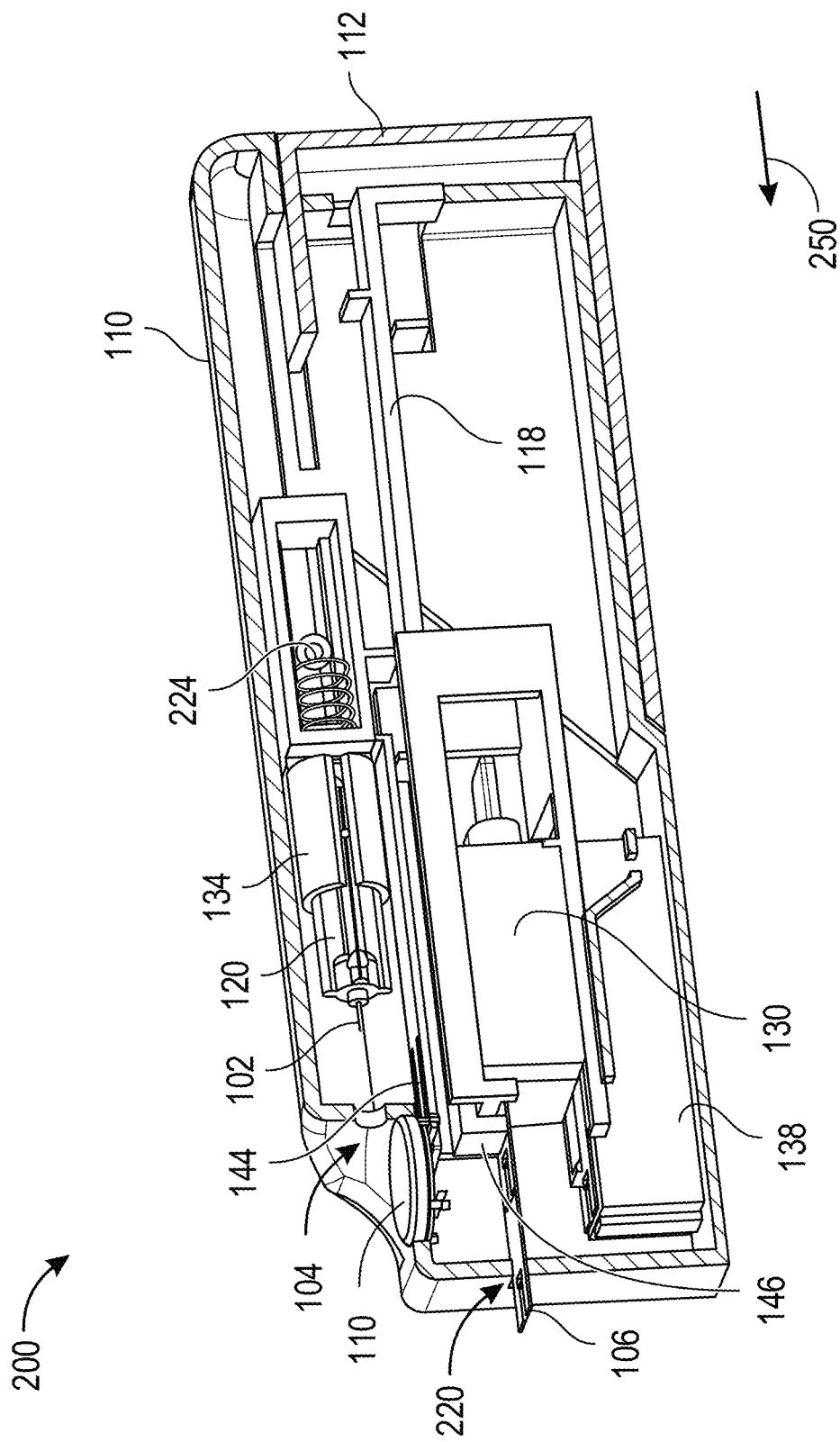
Figures 2, 2D:
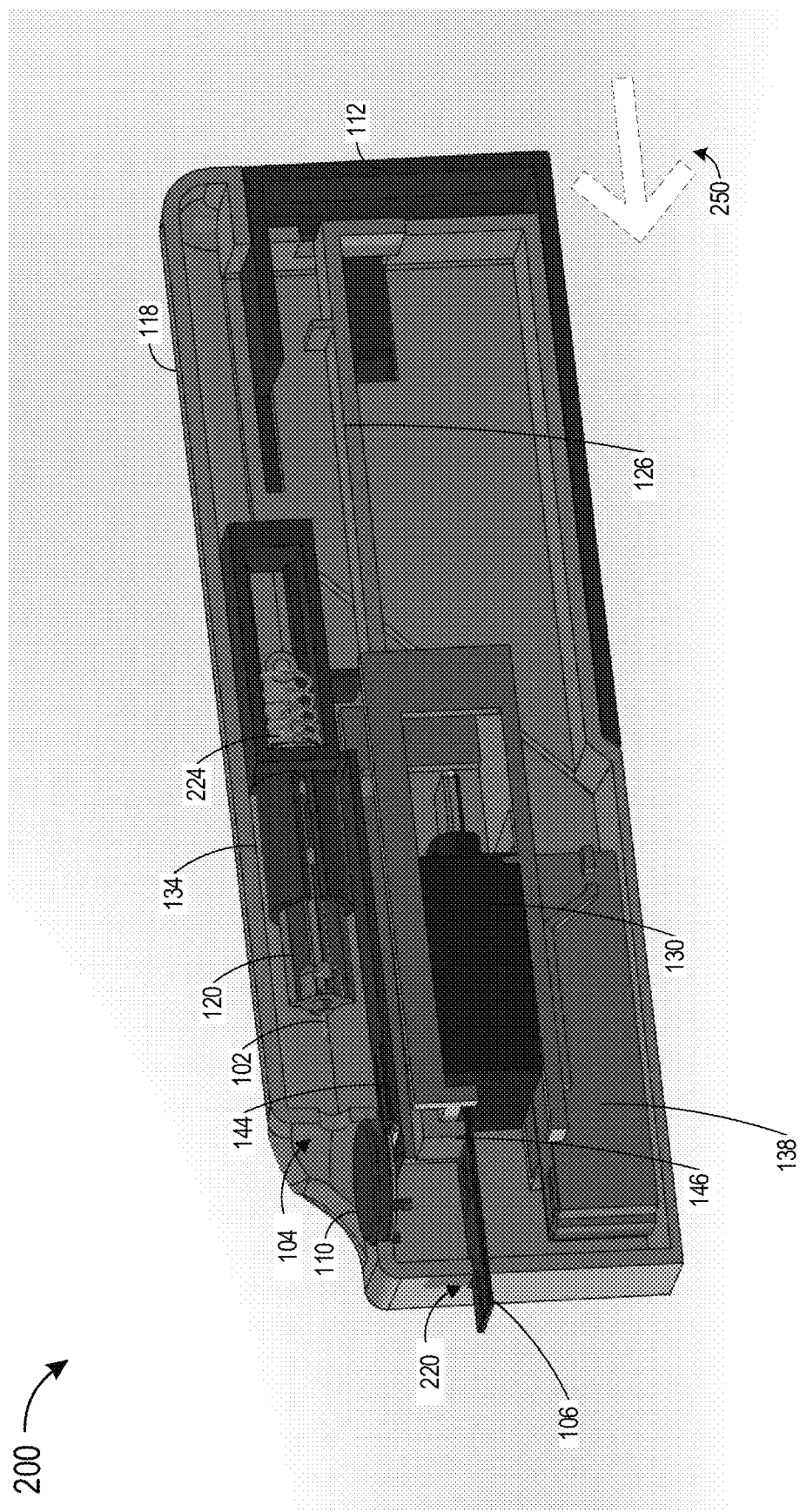

As shown in FIG. 2D, as the user pushes the slider 112 in the second direction 250, toward its forward position, the forward motion (in the second direction 250) of the slider 112 causes the testing strip cartridge 138 to drop down and causes the strip reader frame 142 to move in the second direction 250. Furthermore, a portion 146 of the slider 112 moves the top testing strip 106 of the cartridge 138 forward, towards the testing strip exit hole 220, thereby revealing the testing strip 106 to the outside of the device 100.

FIG. 2D illustrates a cross-sectional view of the device 200 in a loaded or ready state. For example, the user can press the trigger 110 with part of her finger against or proximate to the finger alignment wall 104, and the lancet 102 will prick the finger, as described herein. Once blood is present, the user can then move her finger a small distance to place the blood drop directly on to the revealed testing strip 106. Once the user presses the trigger 110 and uses the testing strip 106, the device 200 again resides in the beginning or unloaded state, as shown in FIG. 2A.

Flow Diagrams

Figure 3:
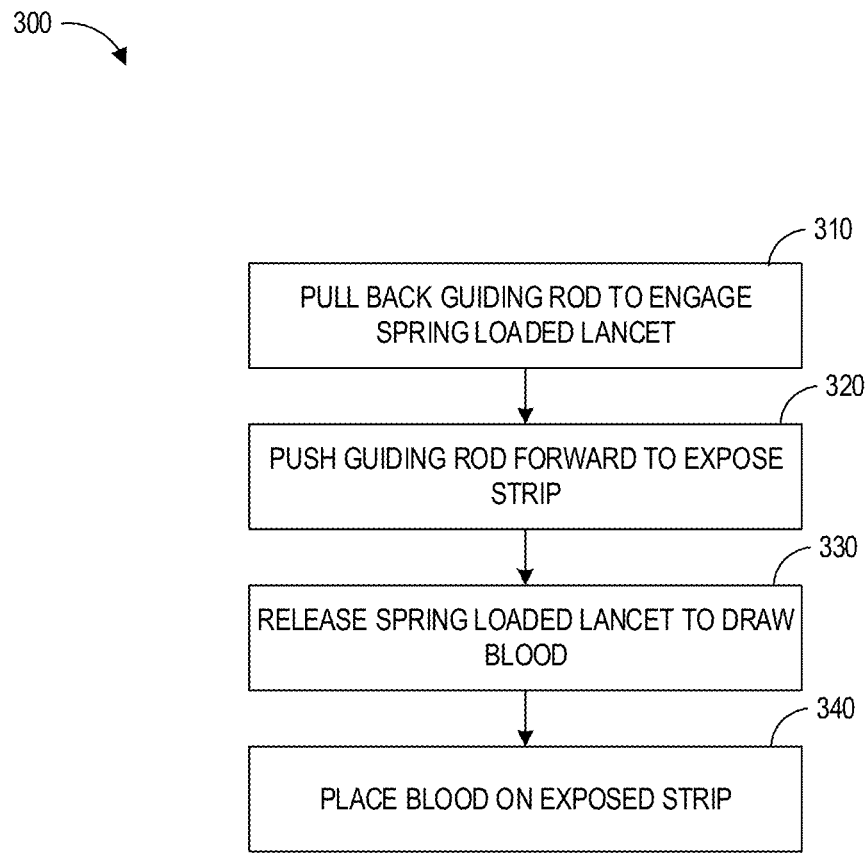
FIG. 3 illustrates an example flow diagram for interacting with an invasive blood constituent device.

FIG. 3 is a flow diagram illustrative of an example of a routine 300 performed by a user for interacting with an invasive blood constituent device. The elements outlined for routine 300 can be implemented by a user of any invasive blood constituent device disclosed herein, such as the invasive blood constituent device 100 of FIGS. 1A-1D or the invasive blood constituent device 200 of FIGS. 2A-2D. For ease of reference, routine 300 has been logically associated to the invasive blood constituent device 200 of FIGS. 2A-2D. However, the following illustrative embodiment should not be construed as limiting. Furthermore, it will be understood that an invasive blood constituent device can include few, more, or additional components to what is describe, which could affect the order or implementation of one or more steps of the routine 300.

At block 310, the user causes the lancet 102 to become spring-loaded. In some cases, to spring-load the lancet 102, the user may slide the slider 112 in a first direction. As the slider is pulled in the first direction, the slider 112 causes the strip guiding rod 222 to also move in the first direction. This movement by the strip guiding rod 126 causes the lancing spring 224 to become compressed, thereby spring-loading the lancet 102.

At block 320, the user causes the invasive blood constituent device 200 to reveal a testing strip 106 from its testing strip exit hole 220. In some cases, to reveal the testing strip 106, the user slides the slider 112 in a second direction, which can be opposite the first direction, such that the slider 112 is back in its forward position. As described herein, pushing the slider 112 forward also pushes the strip guiding rod 126 forward, causing the strip guiding rod 126 to push the testing strip 106 out the testing strip exit hole 220.

At block 330, the user places her finger against or proximate to the finger alignment wall 104 and activates the lancet 102 to prick her finger. As described, to activate the lancet 102, the user can press the trigger 110, causing the lancing spring 224 to unload and launch the lancet 102 to prick her finger.

At block 340, once blood is present, the user moves her finger a small distance to place a blood drop on to the testing strip 106.

Example Strip-Lancet Apparatus

Users of SMBG systems often require numerous disposable components, such as testing strips and lancets, to facilitate the drawing of whole blood and collecting a sample. These components are often handled individually by users, potentially multiple times per day, before being disposed of. In practice, disposing of the components, particularly the lancets, can pose a safety hazard.

A strip-lancet apparatus can combine the roles of two disposable products—a testing strip and a lancing needle—into an apparatus that can be configured for piercing the testing site and then receiving the blood sample. In this way, the strip-lancet apparatus can streamline the process for SMBG, for example by reducing the required number of distinct components. For example, a single strip-lancet apparatus can be use instead of a testing strip and a lancing needle. In addition or alternatively, the disclosed strip-lancet apparatus can facilitate safer disposal practices. For example, the strip-lancet apparatus can include a retractable feature of the lancing needle, which can reduce the likelihood that users will inadvertently prick themselves when disposing of the apparatus.

Figure 5A:
FIGS. 5A and 5B illustrate side pictorial view of an example strip-lancet apparatus.
Figure 5B:

FIGS. 5A and 5B illustrate perspective views, and FIGS. 6A and 6B illustrate pictorial representations of side views, of an example strip-lancet apparatus 500. As shown, the strip-lancet apparatus 500 can be implemented as a relatively flat strip that includes a plurality of layers. A first layer 402 can include a lancet 102 for pricking skin at a measurement site and a second layer 404 can include a testing strip 106 for accepting a blood sample. As shown, the first layer 402 and the second layer 404 can be relatively rectangular. However, it will be understood that the strip-lancet apparatus 500 can be implemented in various ways, including various shapes and sizes. Furthermore, the strip-lancet apparatus 500 can have multiple configurations, as describe herein.

Figure 4A:
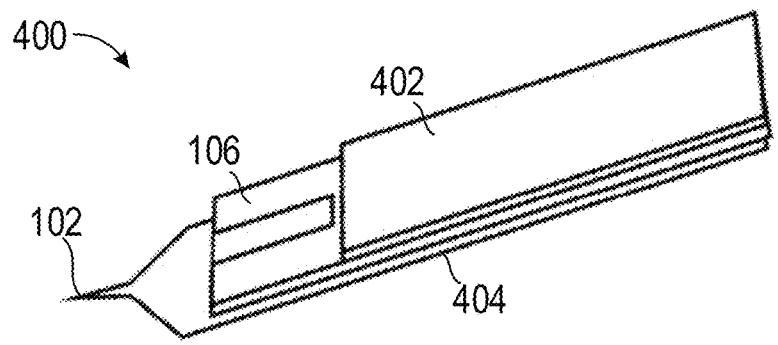
FIGS. 4A and 4B illustrate perspective views of an example strip-lancet apparatus.

FIGS. 4A and 5A illustrate a first configuration of the strip-lancet apparatus 400 in which the lancet 102 extends or protrudes from the strip-lancet apparatus 400 and is exposed to a user. In this example, the first layer 402 is shifted relative to the second layer 402 such that the first layer 402 extends past the edge of the second layer 402.

Figure 4B:
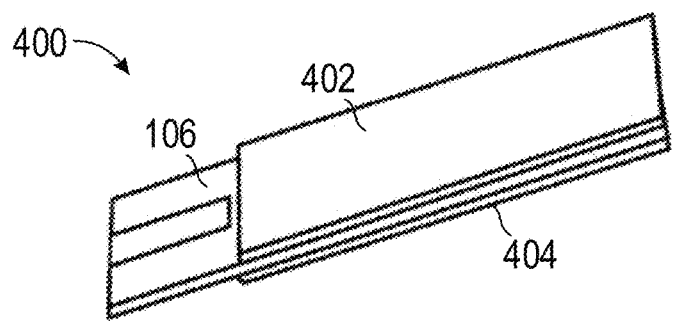

FIGS. 4B and 5B illustrate a second configuration of the strip-lancet apparatus 400 in which the lancet 102 is isolated from the user. For example, in the second configuration, the first layer 602 can be aligned with the second layer 604 such that the second layer 604 covers or protects the lancet 102.

In some cases, the strip-lancet apparatus can transition from the first layer 402 to the second layer 404 and/or the second layer 404 to the first layer 402.

For example, the strip-lancet apparatus can transition from the first configuration to the second configuration responsive to a force applied on the first layer 402 by a launching mechanism. For example, FIGS. 5A and 5B illustrate a launching spring 502. When loaded, the launching spring 502 can be released to slide or push the first layer 402 out and expose the lancet 102. It will be understood that the launching mechanism can vary across embodiments.

Further, in some cases, the strip-lancet apparatus can transition from the second configuration to the first configuration responsive to a force applied on the first layer 402 by a recoil mechanism. For example, FIGS. 5A and 5B illustrate a recoil spring 504. When stretched, the recoil spring 504 can respond by retracting the first layer 402 and/or the lancet 102. In some such cases, the recoil spring 504 can be stretched responsive to the decompressed of the launching spring 502. In this way, the first layer 402, and thus the lancing needle 102, are only temporarily exposed.

In some cases, the strip-lancet apparatus can be configured such that a user rarely handles it when the lancing needle is exposed. For example, the strip-lancet apparatus can include a retractable lancet feature that ensures the lancing needle is isolated from the user, except for a limited amount of time during which it is used to prick the measurement site. In this way, the strip-lancet apparatus can improve the user's safety.

In some cases, an invasive blood constituent device, such as the invasive blood constituent device 100 of FIGS. 1A-1D or the invasive blood constituent device 200 of FIGS. 2A-2D, can include a plurality of strip-lancet apparatuses. For example, the strip-lancet apparatus 400 could be ejected or launched from a device and then left at the site until the blood sample draws into the well. Furthermore, the strip-lancet apparatus 400 could be arranged in a replaceable cartridge that can hold several strips.

In one embodiment the strip could be customized in a smaller size or form factor. Furthermore, in some cases, the strip-lancet apparatus may not be a strip. For example, the strip-lancet apparatus have a needle-like appears that draws blood into the well of the needle.

ADDITIONAL EXAMPLES

Disclosed herein are additional examples of systems and methods described herein. Any of the disclosed examples may be combined in whole or in part.

Example 1: An invasive blood constituent device comprising:
  a trigger;
  a testing strip;
  a lancet; and
  a slider,
wherein a predefined movement of the slider causes the device to load the lancet and/or present the testing strip, Example 2: wherein activation of the trigger after loading the lancet causes the device to activate the lancet, wherein activation of the lancet causes the lancet to prick a measurement site of a user.

Example 3: The device of Example 1, wherein the predefined movement comprises sliding the slider in a first direction and/or sliding the slider in a second direction.

Example 4: The device of Example 2, wherein said sliding the slider in the first direction causes the device to load the lancet, wherein said sliding the slider in the second direction causes the device to present the testing strip.

Example 5: The device of any of the previous examples, further comprising a lancing spring, wherein loading the lancet comprises compressing the lancing spring, wherein activation of the lancet comprises decompressing the lancing spring.

Example 6: The device of any of the previous examples, further comprising:
  a testing strip cartridge comprising a plurality of stacked testing strips, wherein the plurality of stacked testing strips comprises the testing strip; and
  a strip guiding rod,
  wherein the predefined movement of the slider causes the strip guiding rod to move the testing strip from the plurality of stacked testing strips and present the testing strip.

Example 7: The device of any of the previous examples, further comprising:
  a testing strip disposal bin configured to store testing strips,
  wherein the predefined movement of the slider causes the device to add a used testing strip to the testing strip disposal bin.

Example 8: The device of any of the previous examples, further comprising:
  a lancet cartridge comprising a plurality of lancets, wherein the plurality of lancets comprises the lancet,
  wherein the predefined movement of the slider causes the device to select the lancet from the lancet cartridge and load the lancet.

Example 9: The device of any of the previous examples, further comprising:
  a lancet disposal bin configured to store lancets,
  wherein the predefined movement of the slider causes the device to add a used lancet to the lancet disposal bin.

Example 10: The device of any of Examples 6-8, wherein the testing strip disposal bin is the same container as the lancet disposal bin.

Example 11: The device of any of the previous examples, wherein a user places a blood sample on the testing strip.

Example 12: The device of any of the previous examples, further comprising a glucometer configured to obtain data from the blood sample on the testing strip.

Example 13: A method of using an invasive blood constituent device comprising:
  sliding a slider of an invasive blood constituent device according to a predefined movement, said sliding the slider in the predefined movement causes the device to load the lancet and/or present the testing strip; and
  after loading the lancet, activating a trigger of the invasive blood constituent device, wherein activation of the trigger after loading the lancet causes the device to activate the lancet, wherein activation of the lancet causes the lancet to prick a measurement site of a user.

Example 14: The method of Example 12, wherein the predefined movement comprises sliding the slider in a first direction and/or sliding the slider in a second direction.

Example 15: The method of Example 12, wherein the invasive blood constituent device comprising one or more of the features of the device of any of the previous examples.

Example 16: A testing strip apparatus comprising:
  a trigger;
  a testing strip cartridge comprising a plurality of stacked testing strips; and a strip guiding rod,
  wherein activation of the trigger causes the strip guiding rod to move a testing strip from the plurality of stacked testing strips and present the testing strip to a user.

Example 17: The testing strip apparatus of Example 15, further comprising a testing strip disposal bin configured to store testing strips for later disposal.

Example 18: The testing strip apparatus of Example 15, wherein the activation of the trigger causes a previously used testing strip to move into the testing strip disposal bin.

Example 19: A lancet apparatus comprising:
  a trigger;
  a lancet cartridge comprising a plurality of lancets; and
  wherein activation of the trigger causes the device to select a lancet from the plurality of lancets and load the selected lancet.

Example 20: The lancet apparatus of Example 18, further comprising a lancet disposal bin configured to store lancets for later disposal.

Example 21: The lancet apparatus of Example 19, wherein the activation of the trigger causes a previously used lancet to move into the lancet disposal bin.

Example 22: The lancet apparatus of any of Examples 18-20, wherein activation of the trigger causes the selected lancet to project from the lancet apparatus to prick a measurement site of a user.

Example 23: A strip-lancet apparatus comprising:
a first layer comprising a testing strip for accepting a blood sample; and
a second layer comprising a lancing needle for pricking skin at a measurement site.

Example 24: The strip-lancet apparatus of Example 22, wherein the first layer is configured to move relative to the second layer.

Example 25: The strip-lancet apparatus of any Examples 22 or 23, wherein in a first configuration the lancing needle is exposed to a user, and wherein in a second configuration the lancing needle is isolated from the user.

Example 26: The strip-lancet apparatus of any Examples 22-24, wherein in a first configuration the first layer is offset from the second layer, and wherein in a second configuration the first layer is aligned with the second layer.

Example 27: The strip-lancet apparatus of any Examples 22-25, wherein to transition from the first configuration to the second configuration, the first layer is shifted relative to the second layer.

Example 28: The strip-lancet apparatus of any Examples 22-26, wherein the first layer is retractable relative to the second layer.

Example 29: The strip-lancet apparatus of any Examples 22-27, wherein the second layer is retractable relative to the first layer.

Example 30: The strip-lancet apparatus of any Examples 22-28, wherein the strip-lancet apparatus transitions from the second configuration to the first configuration responsive to force applied on the first layer by a launching mechanism.

Example 31: The strip-lancet apparatus of Example 29, wherein the launching mechanism is a spring.

Example 32: The strip-lancet apparatus of any Examples 22-30, wherein the strip-lancet apparatus transitions from the first configuration to the second configuration responsive to force applied on the first layer by a recoil mechanism.

Example 33: The strip-lancet apparatus of Example 31, wherein the recoil mechanism is a spring.

Example 34: The strip-lancet apparatus of any of the Examples 29-32, wherein a direction of the force applied on the first layer by the launching mechanism is opposite to a direction of the force applied on the first layer by the recoil mechanism.

Example 35: The strip-lancet apparatus of any Examples 22-33, wherein the strip-lancet apparatus is rectangular.

Example 36: A strip-lancet apparatus comprising:
a lancing needle for pricking skin at a measurement site; and
a testing strip for accepting a blood sample,
wherein in a first configuration the lancing needle protrudes from an edge of the strip-lancet apparatus, and wherein in a second configuration the strip-lancet apparatus is recoiled into the strip-lancet apparatus.

Example 37: An invasive blood constituent device, a testing strip apparatus, a lancet apparatus, and/or a strip-lancet apparatus as illustrated and/or described.

Example 38: A method of using any of the apparatuses, systems, or devices of any of Examples 1-24.

Example 39: A method of operating an invasive blood constituent device, a testing strip apparatus, a lancet apparatus, and/or a strip-lancet apparatus of any of claims 1-24, as illustrated, and/or described.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The foregoing description is merely illustrative in nature and is in no way intended to limit the disclosure, its application, or uses. For purposes of clarity, in some cases, the same reference numbers will be used in the drawings to identify similar elements. It should be understood that steps within a method may be executed in different order without altering the principles of the present disclosure.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (non-limiting example: not all are necessary for the practice of the algorithms). Moreover, in certain embodiments, operations, acts, functions, or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based at least in part on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based at least in part on the language employed in the claims and not limited to the examples described in the present specification or during the prosecution of the application, which examples are to be construed as non-exclusive.

What is claimed is:

1. An invasive blood constituent device comprising:
    a trigger;
    a testing strip;
    a lancet; and
    a slider, the slider configured to, upon sliding in a first direction, cause the device to load the lancet, and the slider configured to, upon sliding in a second direction, cause the device to present the testing strip,
    wherein activation of the trigger after loading the lancet causes the device to activate the lancet, wherein activation of the lancet causes the lancet to prick a measurement site of a user.

2. The device of claim 1, further comprising a lancing spring, wherein loading the lancet comprises compressing the lancing spring, wherein activation of the lancet comprises decompressing the lancing spring.

3. The device of claim 1, further comprising:
    a testing strip cartridge comprising a plurality of stacked testing strips, wherein the plurality of stacked testing strips comprises the testing strip; and
    a strip guiding rod,
    wherein the sliding of the slider in the second direction causes the strip guiding rod to move the testing strip from the plurality of stacked testing strips and present the testing strip.

4. The device of claim 1, further comprising a glucometer configured to obtain data from a blood sample on the testing strip.

5. A method of using an invasive blood constituent device comprising:
    sliding a slider of the invasive blood constituent device in a first direction to cause the invasive blood constituent device to load a lancet;
    sliding the slider in a second direction to cause the invasive blood constituent device to present a testing strip; and
    after loading the lancet, activating a trigger of the invasive blood constituent device, wherein activation of the trigger after loading the lancet causes the device to activate the lancet, wherein activation of the lancet causes the lancet to prick a measurement site of a user.

6. The method of claim 5, further comprising loading a lancing spring, wherein loading the lancet comprises compressing the lancing spring, and wherein activating the trigger decompresses the lancing spring.

7. The method of claim 5, the invasive blood constituent device comprising:
    a testing strip cartridge comprising a plurality of stacked testing strips, wherein the plurality of stacked testing strips comprises the testing strip; and
    a strip guiding rod,
    wherein sliding the slider in the second direction causes the strip guiding rod to move the testing strip from the plurality of stacked testing strips and present the testing strip.

8. The method of claim 5, further comprising receiving, using the testing strip, a blood sample from the user.

9. The method of claim 8, further comprising obtaining data from the blood sample on the testing strip.

10. The method of claim 9, wherein the obtaining data is performed by a glucometer of the invasive blood constituent device.

* * * * *